United States Patent [19]

Kilejian

[11] Patent Number: 5,439,466

[45] Date of Patent: Aug. 8, 1995

[54] CIRCUMCISION DEVICE AND METHOD OF ITS USE

[76] Inventor: V. John Kilejian, 1694 E. McAndrews Rd., Medford, Oreg. 97504

[21] Appl. No.: 197,876

[22] Filed: Feb. 17, 1994

[51] Int. Cl.⁶ ............................................. A61B 19/00
[52] U.S. Cl. ....................................... 606/118; 606/1
[58] Field of Search ............ 606/118, 1, 167, 135–137, 606/110–112

[56] References Cited

U.S. PATENT DOCUMENTS

| | | |
|---|---|---|
| 1,440,574 | 1/1923 | Ziegler . |
| 2,353,647 | 7/1944 | Carmichael . |
| 2,695,616 | 11/1954 | Hansell . |
| 3,111,124 | 11/1963 | Rodbard . |
| 3,612,057 | 10/1971 | Freedman . |
| 3,741,215 | 6/1973 | Ayad ................................ 606/118 |
| 4,491,136 | 1/1985 | LeVeen .............................. 606/118 |
| 4,938,215 | 7/1990 | Schulman et al. . |
| 5,163,943 | 11/1992 | Mohiuddin et al. . |
| 5,254,125 | 10/1993 | Porter et al. ....................... 606/135 |

Primary Examiner—Peter A. Aschenbrenner
Assistant Examiner—Glenn Dawson
Attorney, Agent, or Firm—Jacobson, Price, Holman & Stern

[57] ABSTRACT

A disposable circumcision device provides quick and accurate alignment of opposite sides of excess prepuce formed by making a dorsal and ventral incision. Two blades compress the excess prepuce against an outer surface of a raindrop ring which protects the glans penis for surgical removal of the excess prepuce. An incision is made by a needle electrode or a knife against the exterior surface of the raindrop ring. The needle electrode or knife is guided along a surface of a dull point of the blade into contact with the exterior surface of the raindrop ring. The precise alignment of the compressed prepuce between the raindrop ring and blade ensures an accurate cut with minimal excess prepuce for subsequent suturing with absorbable sutures. The two prepuce sections formed by a dorsal and ventral incision are tied off at their outermost corners and drawn outwardly by tie lines. The separated halves of the prepuce are then threaded through a space between a ring and two blades of the disposable circumcision device. The blades are then slid along arms of a frame member to crush the prepucial skin between the ring and the blades. Both sides of excess prepuce are removed. The blades are then moved outwardly away from the corona to leave exposed edges of the cut prepuce which are sutured adjacent to the dorsum of the body of the penis.

26 Claims, 4 Drawing Sheets

CIRCUMCISION DEVICE AND METHOD OF ITS USE

FIELD OF THE INVENTION

The present invention relates to a disposable circumcision device and method of its use by which a dorsal and ventral incision of the prepuce allows insertion of separated halves of the prepuce between a raindrop ring and two blades for cutting and removal of excess prepucial skin.

BACKGROUND OF THE INVENTION

Various patents are known for use in circumcision and other surgical procedures such as severing an umbilical cord. These devices provide for exact positioning of an exposed surface, possibly for cutting.

U.S. Pat. No. 3,612,057 to Freedman discloses a circumcision clamp including a pair of concentric plastic rings connected by a radially oriented web. The inner ring is uninterrupted and the outer ring is split adjacent to the web to allow for expansion and contraction of the outer ring relative to the inner ring. The ends of the outer ring include projections for drawing the ring portions together into a clamping position. The foreskin is pulled between the inner and outer rings with the web engaged in a dorsal slit in the foreskin to set the device proximate to the base of the glans. The ends of the outer ring are then drawn together to constrict the outer ring into a clamping position.

U.S. Pat. No. 4,491,136 to LeVeen discloses a disposable circumcision device for cutting of the foreskin of the penis without recourse to sutures. The device includes a male member which covers the head of the penis and a female member which fits over the shaft of the penis. The male member is inserted and fits under the foreskin. The female member fits over the foreskin so that a plastic ring of the female member can be moved up to a position in register which superimposes it over the ring on the male member underneath the foreskin with the foreskin caught in between the two. An external compression member surrounds the plastic flexible ring of the female member for surgical removal of excess foreskin.

U.S. Pat. No. 5,163,943 to Mohiuddin et al. discloses a circumcision instrument with staple means including a pair of body members displaceable toward each other to simultaneously cut the foreskin and stapling together the skin and mucous layers of the foreskin along a stapling line parallel with the cut.

U.S. Pat. No. 2,353,647 to Carmichael discloses an instrument for performing circumcisions which not only assures a bloodless operation but also serves to hold the fore-skin in a fixed circular position to facilitate the cutting operation.

U.S. Pat. No. 2,695,616 to Hansell discloses a circumcision clamp where the prepuce is clamped and crushed in a substantially circular line about the base of the glans to effect hemostasis. This clamp is designed to guard against accidental severing of the frenulum, while, at the same time, facilitating amputation of the prepuce along a line more perfectly conforming to the base contour of the glans.

U.S. Pat. No. 3,111,124 to Rodbard discloses a circumcision clamp that is adjustable in a manner which provides an accurately controlled clamping action which may be relied upon to retain the prepuce under moderate pressure after the circumcision until the blood congeals sufficiently to stop bleeding. The clamp portion is provided with means for applying a partial vacuum within the glans firmly therein without damaging clamping or pressure forces.

U.S. Pat. No. 4,938,215 to Schulman et al. discloses an umbilical cord clamp and cutter device for severing an umbilical cord while maintaining the severed ends thereof in a clamp.

U.S. Pat. No. 1,440,574 to Ziegler discloses an umbilical cord clamp for application to such cord at the time of birth of an infant. The clamp completely squeezes out the moisture from the tissues of the stump of the cord, and keeps the stump elevated and away from the abdomen.

SUMMARY OF THE INVENTION

By the present invention, a disposable circumcision device provides quick and accurate alignment of opposite sides of excess prepuce formed by making a dorsal and ventral incision. Two blades compress the excess prepuce against an outer surface of a raindrop ring which protects the glans penis for surgical removal of the excess prepuce. An incision is made by a needle electrode or a knife against the exterior surface of the raindrop ring. The needle electrode or knife is guided along a surface of a dull point of the blade into contact with the exterior surface of the raindrop ring. The precise alignment of the compressed prepuce between the raindrop ring and blade ensures an accurate cut with minimal excess prepuce for subsequent suturing with absorbable sutures.

The purpose of the oval "RAINDROP" shape of the ring is to allow more accurate alignment along the corona of the penis, as contrasted with a circular ring. The device can also be aligned at an oblique angle along the corona of the penis instead of at a right angle with respect to the shaft of the penis. It is not required to be perpendicular to the axis of the shaft.

By the method of the present invention, a dorsal and ventral incision of the prepuce is made to divide the prepuce into two lateral halves. The two prepuce sections formed are tied off at their outermost corners and drawn outwardly by tie lines. The inventive device with appropriate size ring is chosen. An oval raindrop-shaped ring is slipped over the glans and advanced to just proximal to the corona. It is important to have a tight fit of the ring, snug along the corona. This frees both of the surgeon's hands to manipulate. Each lateral half of the prepuce is brought through the space between the ring and the dull blade and the blades are advanced to hold both halves of the prepuce against the ring. After satisfactory alignment of the ring along the prepuce and optimal natural positioning of the prepuce between the ring and the blade is attained, a bolt is tightened maximally to compress the prepuce against the outer edge of the ring. The excess prepucial skin is then cut with a needle electrode or a knife passed along an upper, distal surface of the blades which extends below an upper surface of the ring. Both sides of excess prepuce are removed.

Tight clamping action of the blade is maintained for 3 to 5 minutes to effect good hemostasis. Reverse counter-clockwise turning of the bolt knob releases the blade and the cut edge of the prepuce. The cut edge is sutured with #5-0 or #4-0 catgut in continuous fashion, or in a manner of the surgeon's choice.

Some of the advantages of this invention over existing devices include:

1. Anatomic considerations, i.e., near perfect alignment of the circumcision line along the corona.
2. Simplicity and ease of manipulation.
3. Virtual absence of bleeding.

The tight fit of the ring around the corona allows fixation of the device and freedom of both of the surgeon's hands. The dull edge of the blade compresses and crushes a thin band of prepuce, thus affording hemostasis. Since the entire procedure takes much less time than a vasectomy, it can easily be performed in an office setting, using local anesthesia and a limited set of instruments.

Another advantage of this device is that by dividing the prepuce in two halves there is complete exposure of the glans, thus permitting its inspection for congenital anomolies prior to removing excess prepucial skin which might be required for future repairs or reconstruction.

It is therefore an object of the present invention to provide a disposable, or with proper sterilization, a permanent circumcision device having a frame with two blade members slidably mounted on the frame for movement towards a centrally-located ring.

It is another object of the present invention to provide a disposable circumcision device having a frame with two blade members slidably mounted on the frame for movement towards a ring with portions of the blade members engaging opposite sides of the arms of the frame.

It is still yet another object of the present invention to provide a disposable circumcision device having a frame with two blade members slidably mounted on the frame for movement towards a centrally-located ring so as to engage dull points of the blade members against opposite sides of the ring so as to crush prepucial skin between the ring and the blades thus causing hemostasis and allowing for cutting and removal of excess prepucial skin by a separate sharp instrument or needle electrode.

It is yet another object of the present invention to practice a method of circumcision using a disposable circumcision device with an initial dorsal and ventral incision of the prepuce and passing of each half of the prepuce through a space between a ring and two blades with the blades being slid into contact with the prepuce to crush the prepucial skin between the ring and the blades allowing for cutting and removal of excess prepucial skin by a separate sharp instrument or needle electrode.

It is still yet another object of the present invention to practice a method of circumcision using a disposable circumcision device with an initial dorsal and ventral incision of the prepuce and passing of each half of the prepuce through a space between a ring and two blades with the blades being slid into contact with the prepuce to crush the prepucial skin between the ring and the blades allowing for cutting and removal of excess prepucial skin with a dull point of the blades providing a guide surface for cutting of excess prepucial skin with a needle electrode or sharp instrument.

These and other objects of the invention, as well as many of the intended advantages thereof, will become more readily apparent when reference is made to the following description taken in conjunction with the accompanying drawings.

DETAILED DESCRIPTION OF THE PREFERRED EMBODIMENTS

Figure 1:
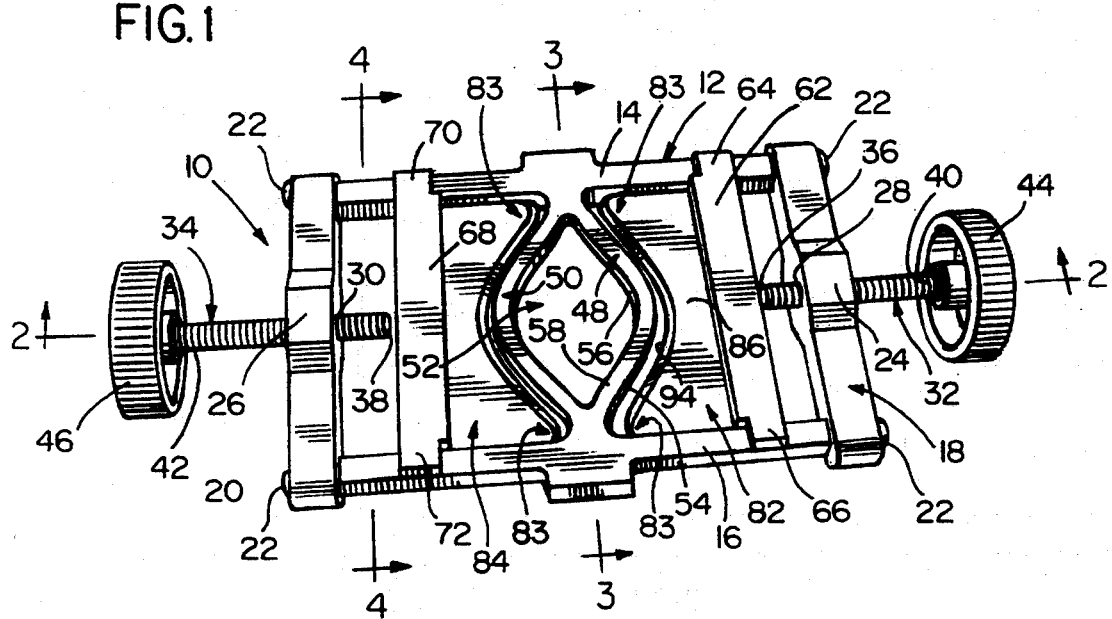
FIG. 1 is a perspective view of a disposable circumcision device.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to the drawings, in general, and to FIGS. 1 through 4, in particular, a disposable circumcision device embodying the teachings of the subject invention is generally designated as 10. With reference to its orientation in FIG. 1, the circumcision device includes a frame 12 comprised of two parallel extending legs 14 and 16 interconnected by two parallel crosspieces 18 and 20 which extend perpendicular to the legs 14 and 16. Cross-piece 18 is secured to legs 14 and 16 by screws 22. Similarly, screws 22 connect cross-piece 20 to an opposite end of legs 14 and 16.

At centrally-located portions of cross-pieces 18 and 20 are enlarged portions 24, 26, respectively, which each include a threaded bore 28, 30. Threaded bores 28, 30 extend parallel to legs 14, 16.

Extending through the threaded bores 28, 30 are threaded shafts 32, 34, respectively, so that an end 36, 38 of the shafts 32, 34 is located within the confines of the frame 12. Located externally of the frame 12 at an opposite end 40, 42, of the shafts 32, 34 are knurled knobs 44, 46, respectively. By rotation of knobs 44, 46 in a clockwise direction, inner ends 36, 38 of the shafts 32, 34 are moved inwardly within frame 12, towards each other.

Integral with and located centrally with respect to a length of the legs 14, 16, are two arms 48, 50 of a raindrop-shaped ring 52. The arms 48, 50 extend between the legs 12 and 14 and are bowed outwardly for receipt of the glans penis. With reference to arm 48, (with identical surfaces of arm 50 being considered similarly identified) opposite sides 54, 56 of the arm 48 extend parallel to each other and at right angles to top surface 58 and bottom surface 60. The overall height of the arms 48 and 50 is approximately ¼ inch.

Figure 4:
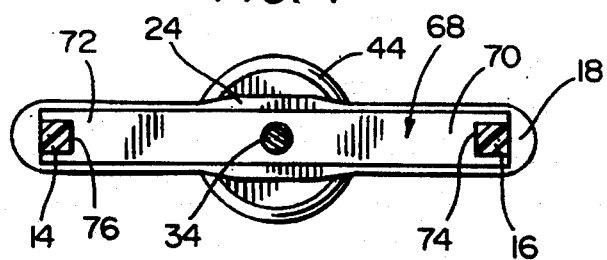
FIG. 4 is a cross-sectional view taken along line 4—4 of FIG. 1.

Slidably mounted between cross-piece 18 and arm 48 is a crossbar 62. Opposite ends 64, 66 of crossbar 62 (as will also apply to crossbar 68), have opposite ends 70, 72, which are C-shaped. As shown in FIG. 4 with respect to crossbar 68, both ends 70 and 72 as well as ends 64, 66 are bifurcated so that within formed channels 74, 76, are received legs 14 and 16 for slidably mounting the crossbars 62 and 68 along the legs 14 and 16. As shown in FIG. 4, a portion of the ends 70, 72 of the crossbar 68 slide along the top and bottom of the legs 14, 16 for a steady slide of the crossbars 62, 68 along the legs 14 and 16.

Figure 2:
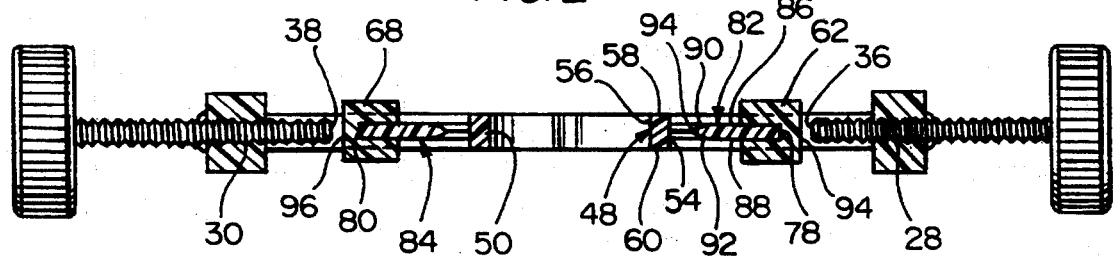
FIG. 2 is a longitudinal sectional view taken along line 2—2 of FIG. 1.
Figure 3:
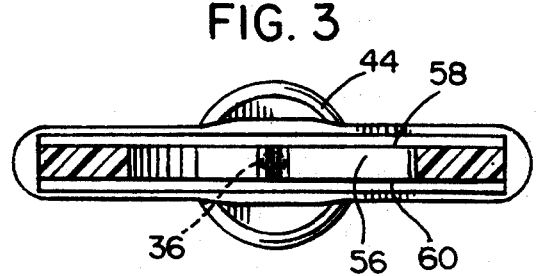
FIG. 3 is a cross-sectional view taken along line 3—3 of FIG. 1.

As shown in FIG. 2, the portion of the crossbars 62, 68 located between the legs 14, 16 includes a slot 78, 80 for receipt of blade 82, 84. Each blade 82, 84 includes an upper surface 86 (with reference to blade 82), and lower surface 88 which extend parallel to each other from the crossbar 62 until immediately adjacent to the arm 48.

At the edge of the blade 82, surfaces 86, 88 taper inwardly along inclined surfaces 90, 92 to form a dull blade point 94 which follows the curvature of the side surface 54 of the arm 48. The thickness of the dull blade 82 as measured between the upper surface 86 and lower surface 88 is approximately $\frac{1}{8}$ inch, or approximately half of the thickness of the arm 48, such that the upper surface 86 of the blades 82, 84 is recessed below the upper surface 58 of the arms 48 and 50. Curved areas 83 at the four "corners" of the blades 84, 86 serves to prevent "bunching" of excess prepuce while compression is occurring.

By the rotation of knobs 44 and 46 in a clockwise direction, as engaged within threaded bores 28 and 30, the ends 36, 38 of the threaded shafts 32, 34 are caused to engage with a sidewall 94, 96 of the crossbars 62, 68 so as to slide the crossbars towards each other. Simultaneously the dull blade point 94 of the two blades 82, 84 is moved towards the arms 48, 50. The importance of this function will be explained with respect to FIG. 10.

Figure 5:
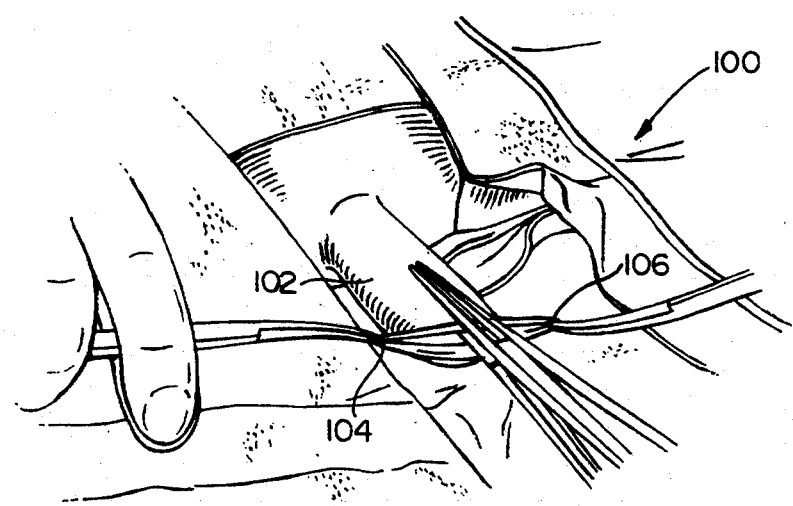
FIGS. 5 through 12 illustrate the various steps of the method of use of the disposable circumcision device shown in FIGS. 1 through 4.

In the method of use of the disposable circumcision device 10 of the present invention, a surgical field 100 is established as shown in FIG. 5. In FIG. 5, the prepuce 102 is grasped from opposite sides at points 104 and 106 to facilitate a dorsal and ventral incision of the prepuce 102.

Figure 6:
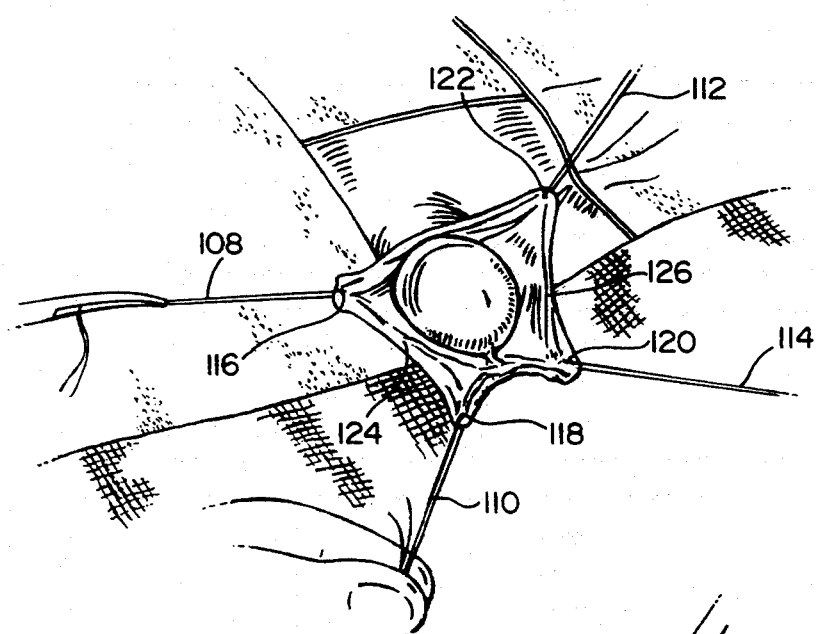

As shown in FIG. 6 after the dorsal and ventral incision, the prepuce 102 is secured by tie lines 108, 110, 112, and 114 through connection points 116, 118, 120, and 122, respectively, so as to spread the prepuce half-sections 124 and 126 away from each other.

Figure 7:
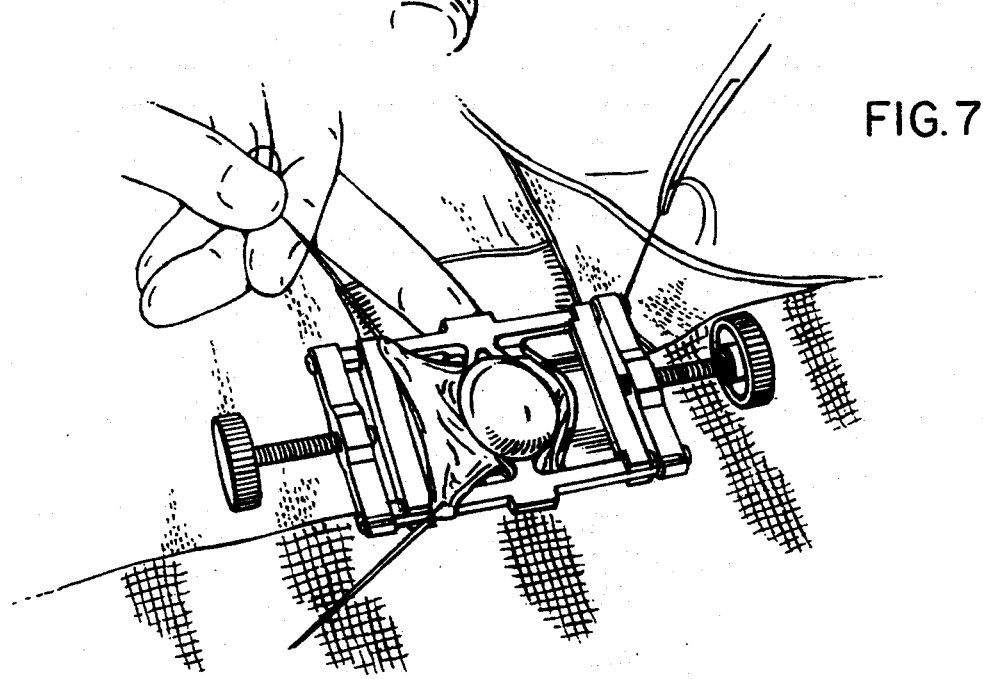
Figure 8:
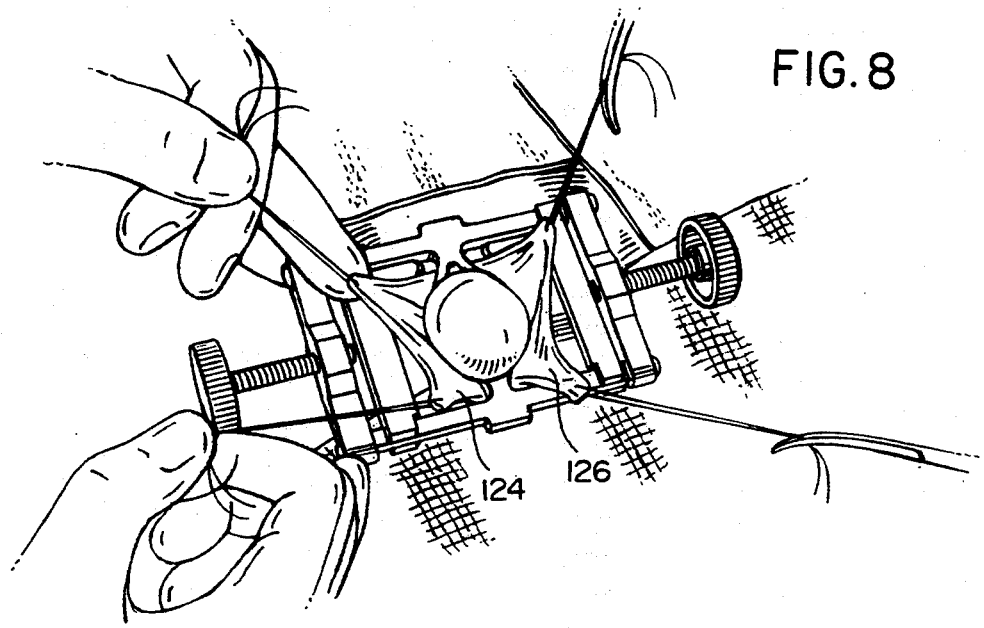

As shown in FIG. 7, prepuce half-section 124 is passed between dull point 94 of blade 84 and outer surface 54 of arm 50. Similarly, as shown in FIG. 8, prepuce half-section 126 will be passed between dull point 94 of blade 82 and outer surface 54 of arm 48.

An appropriately-sized raindrop-shape opening 52 will be selected to fit around the corona of the penis to be operated on and allow for the prepuce half-sections 124, 126 to be threaded between the ring 52 and the blades 82 and 84. After passage of the prepuce half-sections between the blades 82, 84 and the ring 52, the tie lines 108, 110, 112 and 114 will again be stretched taut.

Figure 9:
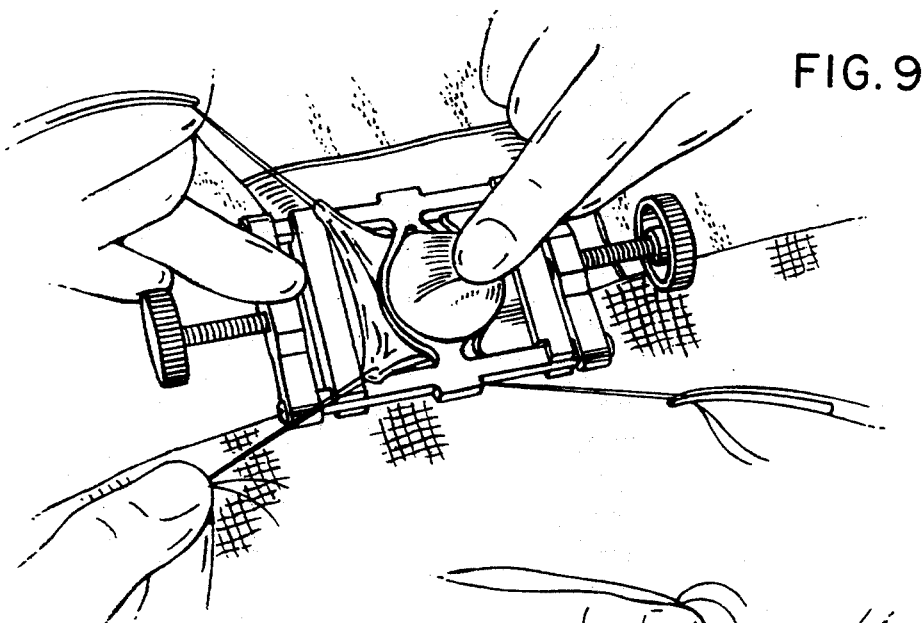

Inspection of the prepuce half-sections is accomplished as shown in FIG. 9, by manual movement of the corona, to ensure that all portions of the prepuce half-section have been threaded through the opening between the blades 82, 84 and the ring 52 and the accurate positioning of the ring 52 along the corona of the penis.

Figure 10:
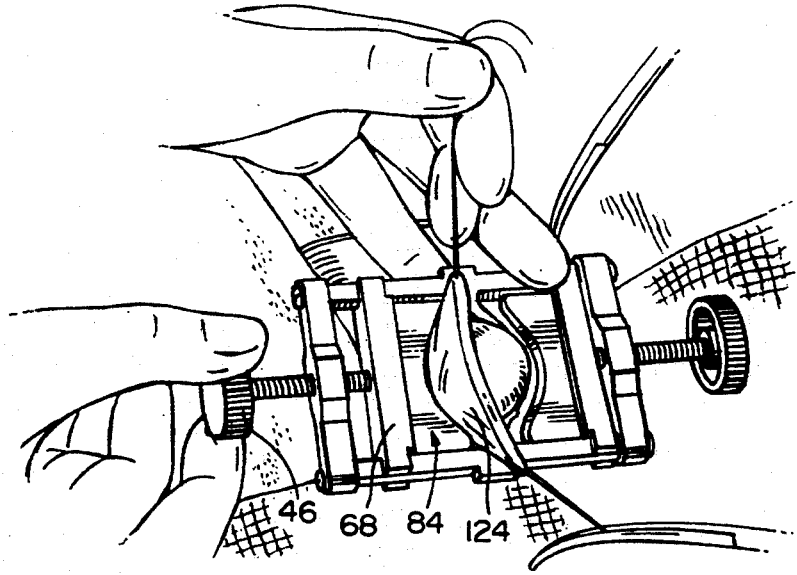

Then, as shown in FIG. 10, knob 46 is turned clockwise so that end 38 of shaft 34 engages side 96 of crossbar 68 so as to slide crossbar 68 in the direction of side 54 of arm 50. The dull point 94 of the blade 84 will thereby crush the prepucial skin between the ring 52 and the blade 84. In FIG. 10, the prepuce half-section 126 has been omitted for clarity.

Figure 11:
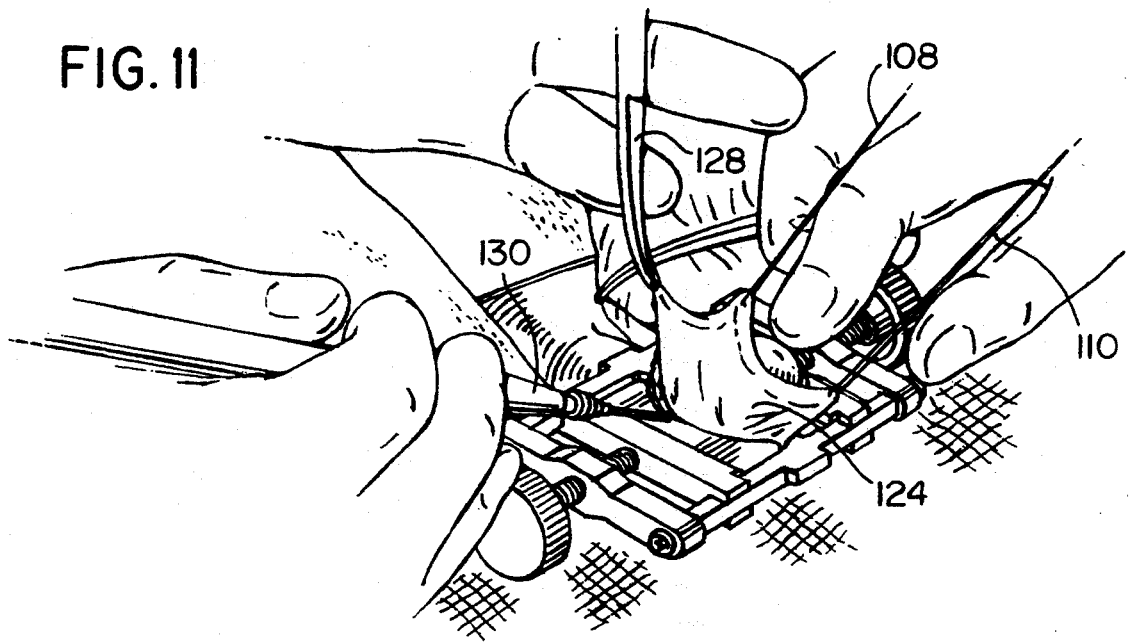
Figure 12:
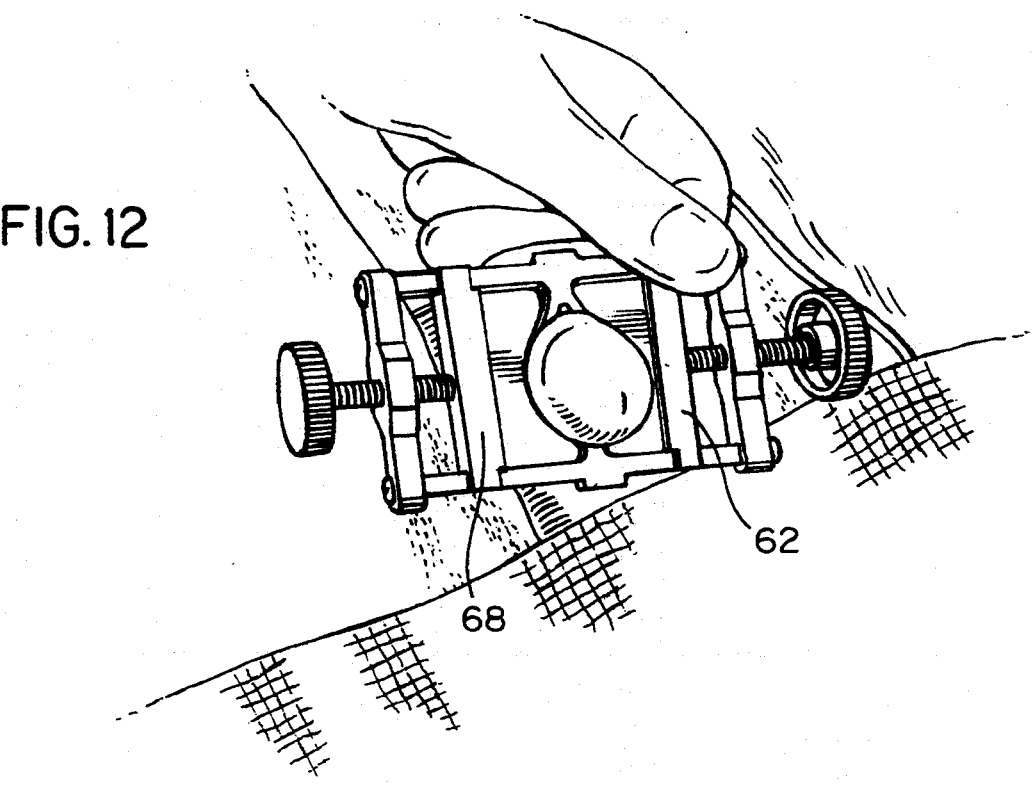

As shown in FIG. 11, by the tensioning of the tie lines 108, 110, as well as any additional assistance as may be required, as indicated by the tweezers 128, the prepuce half-section 124 is tensioned and a needle electrode 130 or knife is used to cut the prepuce half-section 124 for removal. Since the upper surface 86 of the blade 84 is recessed below the upper surface 58 of the arm 50, the outerside surface 54 of the arm 50 is engaged by the needle electrode or knife during the cutting process. By moving the edge of the needle electrode or the cutting edge of a knife along the upper surface 86 and along the downwardly-inclined surface 90 of the blade 82, an incision on the prepuce half-section is performed which maximizes prepuce removal adjacent to the dorsum of the body of the penis, below the lower edge of the glans of the penis as shown in FIG. 12. The knobs 44, 46 can then be rotated counterclockwise and the crossbars 62, 68 moved away from the glans penis for removal of the device and for suturing the edges of the cut prepuce with absorbable sutures. The circumcision device 10 is then intended to be discarded.

Having described the invention, many modifications thereto will become apparent to those skilled in the art to which it pertains without deviation from the spirit of the invention as defined by the scope of the appended claims.

I claim:

1. A circumcision device comprising:
   a frame,
   a ring located in said frame for surrounding the glans penis during a circumcision operation,
   two blades slidably mounted in said frame, and
   means for moving said two blades towards said ring to engage portions of the prepuce of the penis between exterior surfaces of said ring and leading edges of said two blades during a circumcision operation so as to provide guide surfaces for cutting the portions of the prepuce with minimal amounts of prepuce remaining after completion of the circumcision operation,
   said frame including two parallel extending legs and two parallel extending cross-piece with said two cross-pieces extending perpendicular to said two legs.

2. A circumcision device as claimed in claim 1, wherein said ring is connected to said two legs.

3. A circumcision device as claimed in claim 2, wherein said ring includes two arms extending between said two legs.

4. A circumcision device as claimed in claim 3, wherein said two arms are curved with said leading edge of said two blades being curved complementary to said two arms.

5. A circumcision device as claimed in claim 1, wherein said means for moving includes two shafts for engaging said two blades.

6. A circumcision device comprising:
   a frame including two legs,
   a ring connected to said two legs,
   two blades slidably mounted on said two legs on opposite sides of said ring, said two blades having dull leading edges, and said dull
   means for moving said two blades towards said ring to engage portions of the prepuce of the penis between exterior surfaces of said ring and leading edges of said two blades during a circumcision operation so as to provide guide surfaces for cutting the portions of the prepuce with minimal amounts of prepuce remaining after completion of the circumcision operation.

7. A circumcision device as claimed in claim 6, wherein corners of said two blades at said dull leading edges are curved to prevent bunching of excess prepuce during compression of the prepuce.

8. A method of circumcising a penis, said method comprising:

cutting the prepuce into two portions, locating the glans penis within a ring, passing the two portions of the prepuce between two blades and the ring, moving the two blades towards the ring so as to compress the two portions of the prepuce between an exterior surface of the ring and a dull leading edge of each of the two blades, cutting the two portions of the prepuce along an upper surface of the two blades so as to separate the prepuce from the penis.

9. A method of circumcising a penis as claimed in claim 8, wherein the prepuce is cut into two portions by a dorsal and a ventral incision.

10. A method of circumcising a penis as claimed in claim 8, wherein the two blades are moved by sliding along a frame within which the ring is also mounted.

11. A method of circumcising a penis as claimed in claim 8, wherein the cutting of the two portions of the prepuce is guided by a downwardly inclined surface located adjacent each drill leading edge of the blades.

12. A method of circumcising a penis as claimed in claim 8, wherein the ring is centrally located between the two blades.

13. A circumcision device comprising:

a frame, a ring located in said frame for surrounding the glans penis during a circumcision operation, two blades slidably mounted in said frame, said two blades having dull leading edges, and means for moving said two blades towards said ring to engage portions of the prepuce of the penis between exterior surfaces of said ring and said leading edges of said two blades during a circumcision operation so as to provide guide surfaces for cutting the portions of the prepuce with minimal amounts of prepuce remaining after completion of the circumcision operation.

14. A circumcision device as claimed in claim 13, wherein said two blades are fitted within two crossbars slidably mounted on said frame.

15. A circumcision device as claimed in claim 13, wherein corners of said two blades at said leading edges are curved to prevent bunching of excess prepuce during compression of the prepuce.

16. A circumcision device comprising:

a frame including two legs, a ring connected to said two legs, two blades slidably mounted on said two legs on opposite sides of said ring, and means for moving said two blades towards said ring to engage portions of the prepuce of the penis between exterior surfaces of said ring and leading edges of said two blades during a circumcision operation so as to provide guide surfaces for cutting the portions of the prepuce with minimal amounts of prepuce remaining after completion of the circumcision operation, said two blades being fitted within two crossbars slidably mounted on said frame.

17. A method of circumcising a penis, said method comprising:

cutting the prepuce into two portions, locating the glans penis within a ring, passing the two portions of the prepuce between two blades and the ring, moving the two blades towards each other and towards the ring so as to compress the two portions of the prepuce against an exterior surface of the ring by the two blades, cutting the two portions of the prepuce along an upper surface of the two blades so as to separate the prepuce from the penis.

18. A circumcision device comprising:

a frame, a ring located in said frame for surrounding the glans penis during a circumcision operation, two planar blades slidably mounted in said frame and movable in a direction parallel to a flat plane defined by said ring, and means for moving said two blades towards each other and towards said ring to engage portions of the prepuce of the penis between exterior surfaces of said ring and leading edges of said two planar blades during a circumcision operation so as to provide guide surfaces for cutting the portions of the prepuce with minimal amounts of prepuce remaining after completion of the circumcision operation.

19. A circumcision device as claimed in claim 18, wherein said frame includes two parallel extending legs and two parallel extending cross-pieces with said two cross-pieces extending perpendicular to said two legs.

20. A circumcision device as claimed in claim 19, wherein said ring is connected to said two legs.

21. A circumcision device as claimed in claim 20, wherein said ring includes two arms extending between said two legs.

22. A circumcision device as claimed in claim 21, wherein said two arms are curved with said leading edge of said two planar blades being curved complementary to said two arms.

23. A circumcision device as claimed in claim 18, wherein said two planar blades are dull at said leading edges.

24. A circumcision device as claimed in claim 23, wherein said two planar blades are fitted within two crossbars slidably mounted on said frame.

25. A circumcision device as claimed in claim 23, wherein corners of said two planar blades at said leading edges are curved to prevent bunching of excess prepuce during compression of the prepuce.

26. A circumcision device as claimed in claim 18, wherein said means for moving includes two shafts for engaging said two planar blades.

* * * * *